United States Patent
Heckel et al.

(10) Patent No.: US 10,771,167 B2
(45) Date of Patent: Sep. 8, 2020

(54) SYSTEM AND METHODS FOR MITIGATING INTERFERENCES BETWEEN ELECTROSURGICAL SYSTEMS

(71) Applicant: COVIDIEN LP, Mansfield, MA (US)

(72) Inventors: Donald W. Heckel, Thornton, CO (US); William D. Faulkner, Boulder, CO (US); Donald L. Tonn, Superior, CO (US); Fred B. Pelton, Longmont, CO (US)

(73) Assignee: Covidien LP, Mansfield, MA (US)

( * ) Notice: Subject to any disclaimer, the term of this patent is extended or adjusted under 35 U.S.C. 154(b) by 490 days.

(21) Appl. No.: 15/801,656

(22) Filed: Nov. 2, 2017

(65) Prior Publication Data

US 2019/0132062 A1    May 2, 2019

(51) Int. Cl.
  *A61B 18/12*  (2006.01)
  *H04B 15/02*  (2006.01)
  (Continued)

(52) U.S. Cl.
  CPC ......... *H04B 15/02* (2013.01); *A61B 18/1206* (2013.01); *A61B 18/1233* (2013.01);
  (Continued)

(58) Field of Classification Search
  CPC .......... H04B 15/00–06; A61B 18/1206; A61B 18/1233; A61B 2018/00732; A61B 2018/00845; A61B 2018/00875; A61B 2018/00892; A61B 2018/00898; A61B 2018/1293

See application file for complete search history.

(56) References Cited

U.S. PATENT DOCUMENTS 6,269,093 B1    7/2001  Alapuranen et al.
7,300,435 B2   11/2007  Wham et al.
(Continued)

FOREIGN PATENT DOCUMENTS

EP    1055399 A1    11/2000
WO   2016046191 A1   3/2016

OTHER PUBLICATIONS

Extended European Search Report issued by the European Patent Office dated Apr. 3, 2019 in corresponding European Patent Application No. 18203918.

*Primary Examiner* — Daniel W Fowler
(74) *Attorney, Agent, or Firm* — Carter, DeLuca & Farrell LLP

(57) ABSTRACT

Methods and system are provided to mitigate RF interferences during operation of an electrosurgical system. An electrosurgical system configured to output therapeutic RF energy may refrain from outputting RF energy in order to measure an RF interference for a group of candidate frequencies, and to select a frequency from the group of candidate frequencies for which the measured RF interference is below a threshold value, and to produce a feedback signal (a control signal) at the selected frequency to control operation of the electrosurgical system. During operation of the electrosurgical system the feedback signal may be filtered by a BPF whose fundamental frequency is set to the selected frequency, to thus obtain an interference free feedback signal and, consequently, a reliable control of the electrosurgical system.

20 Claims, 8 Drawing Sheets

(51) Int. Cl.
*H04B 17/345* (2015.01)
*A61B 18/00* (2006.01)

(52) U.S. Cl.
CPC .. *H04B 17/345* (2015.01); *A61B 2018/00732* (2013.01); *A61B 2018/00845* (2013.01); *A61B 2018/00875* (2013.01); *A61B 2018/00892* (2013.01); *A61B 2018/00898* (2013.01); *A61B 2018/1293* (2013.01)

(56) References Cited

U.S. PATENT DOCUMENTS

| | | | |
|---|---|---|---|
| 2003/0130711 A1* | 7/2003 | Pearson | A61B 18/1477 607/101 |
| 2004/0015160 A1 | 1/2004 | Lovewell | |
| 2006/0098806 A1 | 5/2006 | Schulz | |
| 2010/0130976 A1* | 5/2010 | Bystryak | A61B 18/1233 606/42 |
| 2010/0168557 A1* | 7/2010 | Deno | A61B 5/053 600/424 |
| 2011/0208183 A1 | 8/2011 | Stockert | |
| 2012/0059436 A1 | 3/2012 | Fontaine et al. | |
| 2014/0316404 A1* | 10/2014 | Neumann | A61B 18/1233 606/34 |
| 2014/0369166 A1 | 12/2014 | McDavid | |
| 2015/0282857 A1* | 10/2015 | Anderson | A61B 18/1206 606/41 |

* cited by examiner

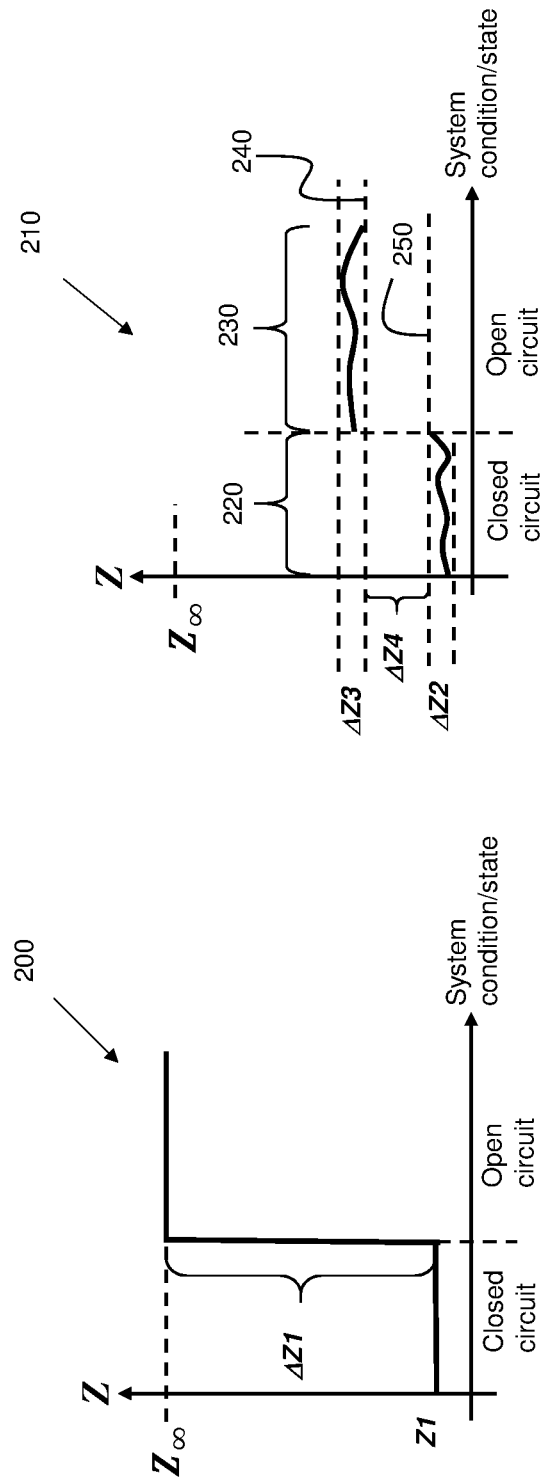

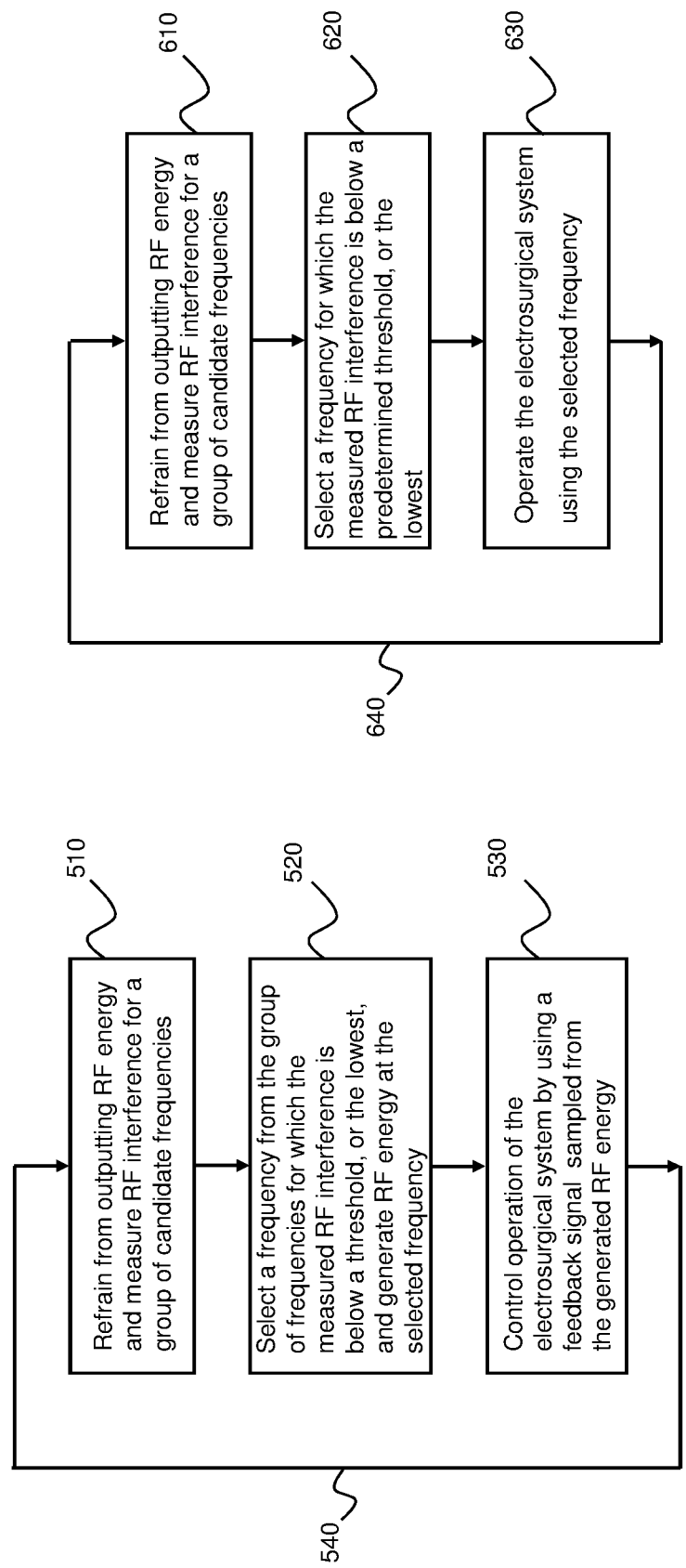

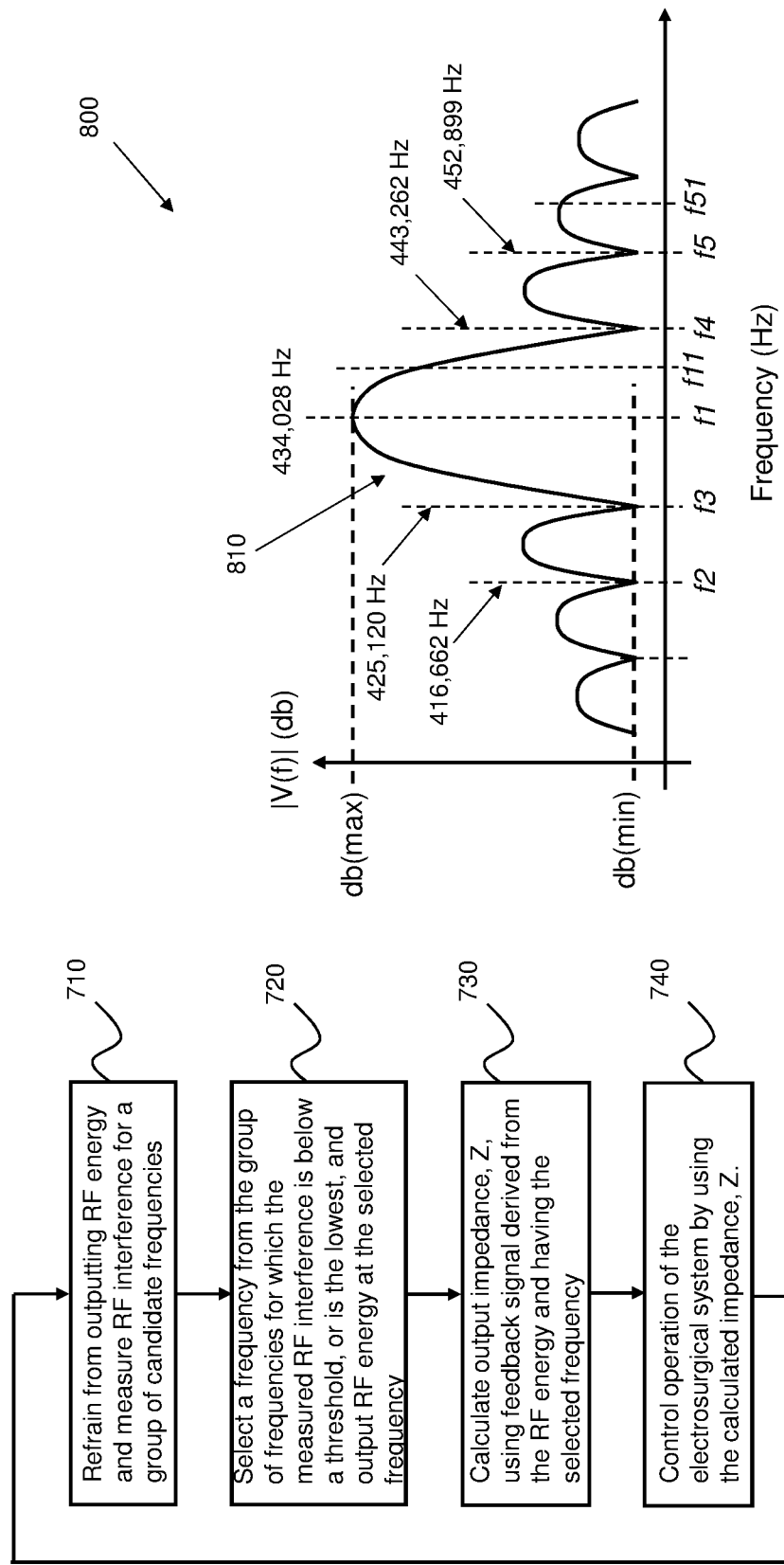

SYSTEM AND METHODS FOR MITIGATING INTERFERENCES BETWEEN ELECTROSURGICAL SYSTEMS

FIELD OF THE INVENTION

The present disclosure relates to electrosurgical systems. More particularly, the present disclosure is directed to methods for reducing radio frequency ("RF") interferences between electrosurgical systems during electrosurgical procedures, and to an electrosurgical system that uses the methods.

BACKGROUND

Surgery is sometimes performed using an energy delivering system. Various types of therapeutic energies (e.g., electrical, RF, ultrasonic, microwave, cryogenic, heat, laser, etc.) may be used to treat a tissue. Electrosurgery is a tissue treating technique involving delivery of high RF electrical energy (e.g., 1-70 watts in bipolar and autobipolar electrosurgical systems, 1-300 watts in monopolar electrosurgical systems). Electrosurgical treatment is rendered by an electrosurgical system via an electrosurgical device (e.g., electrosurgical forceps, a treatment electrode and a dispersive neutral electrode (REM) pad). Electrosurgical RF generators differ widely in their output (energy carrier) RF, which may be approximately between 300 KHz and 480 KHz. There are three main types of electrosurgical systems: monopolar electrosurgical systems, bipolar electrosurgical systems and autobipolar electrosurgical systems.

Each electrosurgical system controls its operation state or mode (including transitioning between states and transitioning between operation modes) by using a feedback signal that is produced from electrical current samples and/or voltage samples that reflect, represent or are derived from the system's output RF energy. Controlling the state or operation mode of an electrosurgical system may include controlling an electrical parameter of the electrosurgical system, for example an electrical current that the electrosurgical system outputs, an electrical voltage that the electrosurgical system outputs or an electrical power of a therapeutic RF energy that the electrosurgical system outputs. Regardless of the type of the electrosurgical system that is used, using a reliable feedback signal is prerequisite to proper operation of the electrosurgical system, and thus to the RF treatment efficacy.

In some instances, conventional electrosurgical systems output therapeutic RF energy by using a same, or a similar, frequency. When two (or more) electrosurgical systems, which use a same, or a similar, carrier RF, treat two sites of a patient at a same time, it may occur that a therapeutic energy, when applied to one site by a first electrosurgical system, would interfere with the feedback signal of another electrosurgical system, and thus with the operation of the other electrosurgical system. One example scenario where two treatment sites are treated at the same time is a medical procedure known as coronary artery bypass grafting ("CABG") which involves cardiac vein harvesting from the leg and implanting the harvested cardiac vein in another site where the vein is needed. In another scenario, a spine may be operated at two surgical sites by using two electrosurgical systems at a same time.

The interference an electrosurgical system may be subjected to is due to a remote therapeutic (high power) RF energy of another electrosurgical system that is superimposed on the feedback signal that is used to control the operation of the interfered with electrosurgical system. The feedback signal and an interfering therapeutic RF energy may jointly be subjected to constructive interference or to destructive interference, which makes the feedback signal susceptible to RF interferences that originate, for example, from other electrosurgical systems and have an identical, or similar, RF frequency. If the frequency of the feedback signal in one electrosurgical system and the frequency of the therapeutic RF energy are close (rather than being identical), alternating constructive interference and destructive interference may produce "beats" in the feedback signal, which would impair (distort, deform) the feedback signal, making it unreliable.

It would, therefore, be beneficial to have methods and system that enable simultaneous and independent operation of multiple electrosurgical systems without the electrosurgical systems interfering with one another during an electrosurgical procedure.

SUMMARY

Methods and system are provided, which mitigate RF interferences during operation of an electrosurgical system. A method, in some embodiments, may include refraining from outputting RF energy and, using a band pass filter ("BPF"), measuring an RF interference for a group of candidate frequencies, selecting a frequency from the group of candidate frequencies for which the measured RF interference is below a threshold value, or the lowest, generating (and optionally outputting) RF energy at the selected frequency, and controlling operation of the electrosurgical system by using a feedback signal that is derived from, or represents, or sampled from the generated or output RF energy and has the selected frequency. Depending on the type of the electrosurgical system and on the system's operation mode, the RF energy that the electrosurgical system outputs may be therapeutic energy or interrogation signal, and the feedback signal may be filtered by a BPF whose center (fundamental) frequency is set to the selected frequency.

Controlling the operation of the electrosurgical system may include, for example, calculating from, or by using, the feedback signal, a value of an operational parameter of the electrosurgical system, and controlling the operation of the electrosurgical system based on the calculated value of the operational parameter. In some embodiments the operational parameter used to control the operation of the electrosurgical system may be an impedance (Z) at the output of the electrosurgical system, and controlling the operation of the electrosurgical system may include controlling an output electric current (I) of the electrosurgical system, or an output electric voltage (V) of the electrosurgical system site, or an electrical power (P) of the RF energy that is output by the electrosurgical system, or any combination thereof.

The electrosurgical system subject of the present invention may be a monopolar electrosurgical system, a bipolar electrosurgical system an autobipolar electrosurgical system, and the like. Each electrosurgical system (regardless of its type) may produce the feedback signal at the selected frequency, and the feedback signal may be derived from the therapeutic RF energy that the electrosurgical system outputs when it operates in the treatment mode. In some cases (for example when the electrosurgical system is an autobipolar electrosurgical system), the feedback signal may be derived from an interrogation signal, or energy, that is generated by the electrosurgical system in an interrogation mode of operation before the electrosurgical system transitions to the treatment mode. The electrosurgical system may transition from the interrogation mode to the treatment mode, and vice versa, based, for example, on the impedance (Z) at the output of the electrosurgical system and/or based on another electrical parameter.

Measuring an RF interference for each particular frequency in the group of candidate frequencies may include, for example, configuring a BPF to pass only signals having the particular frequency. The band pass filter may be implemented as a Goertzel filter, and the frequencies included in the frequency group may be selected such that they satisfy a coherent sampling condition in order for them to coincide with null points in a frequency response (magnitude-frequency curve) of the filter.

In some embodiments a method of mitigating RF interferences during operation of an electrosurgical system may include performing, by an electrosurgical system that is configured to output an RF energy, refraining from outputting RF energy and, while refraining from outputting RF energy, measuring an RF interference for each candidate frequency in a group of candidate frequencies, selecting a frequency from the group of candidate frequencies for which the measured RF interference is below a predetermined threshold, or the lowest and outputting RF energy at the selected frequency, calculating an impedance (Z) at the output of the electrosurgical system by using a feedback signal that is derived from the RF energy and has the selected frequency, and controlling operation of the electrosurgical system by using the calculated impedance (Z).

Controlling the operation of the electrosurgical system may include controlling, during treatment delivery, an output electrical current of the electrosurgical system or an output electrical voltage of the electrosurgical system or an electrical power of the RF energy, or any combination thereof. Controlling the operation of the electrosurgical system may also include determining a state or an operational mode of the electrosurgical system, for example determining, during therapeutic RF energy delivery, whether or when to transition the electrosurgical system from the treatment mode in which the electrosurgical system outputs (high power) therapeutic RF energy, to the interrogation mode in which the electrosurgical system outputs a low power interrogation signal (e.g., to measure impedance at the system's output in order to determine whether or when to transition the electrosurgical system to the treatment mode), and, while operating in the interrogation mode, whether or when to transition the electrosurgical system back to the treatment mode. Controlling the operation of the electrosurgical system may also include controlling an output electric current of the electrosurgical system, an output electric voltage of the electrosurgical system, an output electrical power of the RF energy that the electrosurgical system outputs, and/or determining a state and/or an operation mode of the electrosurgical system.

The electrosurgical system may include an electrosurgical generator to generate therapeutic RF energy, a controller to control the operation of the electrosurgical generator, and a data storage that stores a group of candidate frequencies and parameters and/or coefficients that define, or that enable to configure, a configurable BPF. The controller may be configured to: (i) cause the electrosurgical generator to refrain from outputting RF energy and, while doing that, to measure an RF interference for each frequency in the group of candidate frequencies, (ii) select a frequency from the group of candidate frequencies for which the measured RF interference is below a predetermined threshold, or the lowest, and cause the electrosurgical generator to generate (and, optionally, to output) RF energy at the selected frequency, and (iii) control operation of the electrosurgical system by using a feedback signal that is derived (e.g., sampled) from the generated/output RF energy. (Being derived; e.g., by sampling samples from a generated RF energy, the feedback signal also has the selected frequency.)

The controller may be configured to calculate an impedance (Z) at the output of the electrosurgical system from the feedback signal (e.g., from voltage and current samples), and to control, based on the calculated impedance, an output electric current (I) of the electrosurgical system, or an output electric voltage (V) of the electrosurgical system site, or an electrical power (P) of the RF energy that is output by the electrosurgical system. The controller may use voltage samples or current samples that may be taken from the output RF energy, or both voltage and current samples, to control any electrical parameter (e.g., output current, output voltage, output power) of the RF energy that the related electrosurgical system outputs, and/or to control the state or operation mode of the related electrosurgical system.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 2A shows a plot illustrating ideal situation in the context of impedance evaluation in autobipolar systems;

FIG. 2B shows a plot illustrating interference-free realistic situations in the context of autobipolar systems;

FIG. 5 shows a method for mitigating RF interferences in an electrosurgical system according to an example embodiment;

FIG. 6 shows a method for mitigating RF interferences in an electrosurgical system according to another example embodiment;

FIG. 7 shows a method for mitigating RF interferences in an electrosurgical system according to yet another example embodiment; and FIG. 8 shows an example application of a magnitude-frequency response of a BPF in accordance with an example embodiment.

DETAILED DESCRIPTION

Figure 1A:
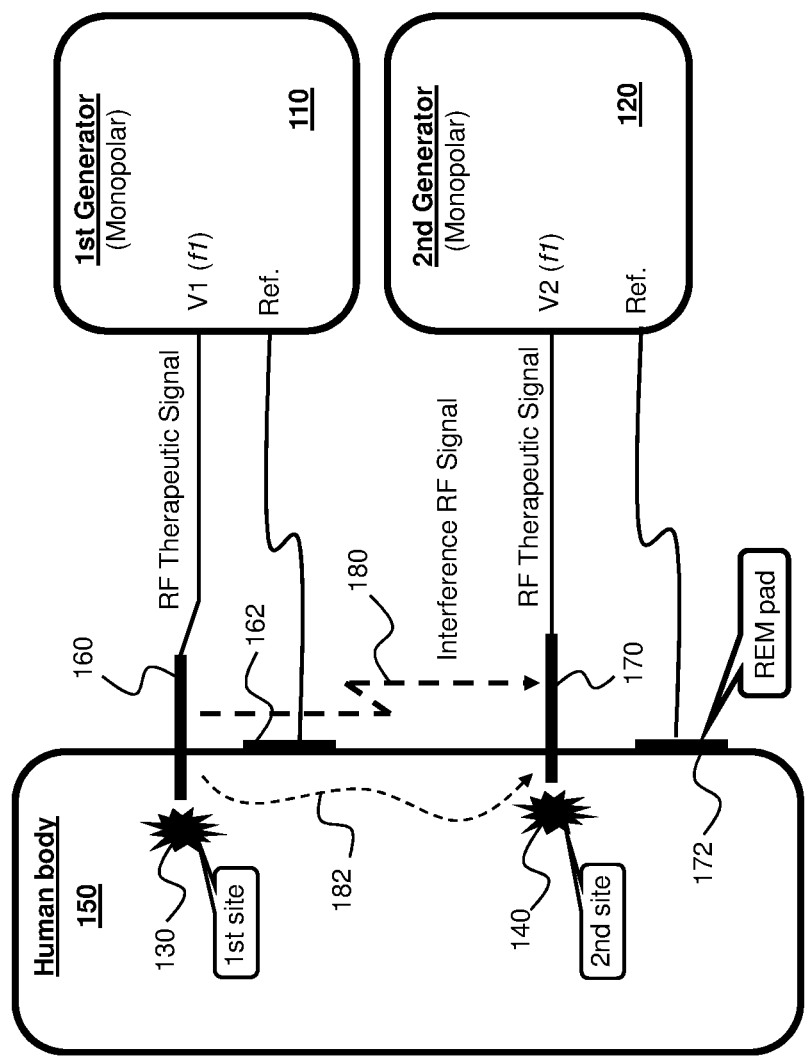
FIGS. 1A and 1B schematically illustrate electrosurgical systems in different electrosurgical treatment setups where operation of one electrosurgical system may interfere with the operation of another electrosurgical system.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining", "estimating", "evaluating", "analyzing", "checking", or the like, may refer to operation(s) and/or process(es) of a computer, a computing system or other electronic computing device (e.g., controller), that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not limited to a particular order or sequence. Additionally, some of the described method embodiments or steps thereof can, for example, occur or be performed at the same point in time.

The present disclosure discloses methods and system for ensuring that a feedback signal, which an electrosurgical system uses for controlling, for example, an operational parameter of the electrosurgical system and/or its operational state or mode of operation, is not affected, or only negligibly affected, by RF interferences originating from a nearby electrosurgical system. Briefly, a group of strictly selected RF frequencies (which are referred to herein as "candidate frequencies") are selected for an electrosurgical system as potential RF carrier frequencies which the electrosurgical system may use to output RF energy, and a suitable candidate frequency (a 'quiet', or the quietest, frequency in terms of RF interferences) may be selected from the frequency group, thus ensuring an interference-free control of the electrosurgical system throughout its operation range and states. If a candidate frequency selected for an electrosurgical system gets noisy (if it is interfered with), a different, quieter (less interfered with), carrier frequency may be selected (from the group of candidate frequencies) for use by the electrosurgical system.

The term "feedback signal", as used herein, may represent any type of signal, data or information that an electrosurgical system may produce from voltage samples and/or from electrical current samples, or from both current and voltage samples of an RF energy that the electrosurgical generator of the electrosurgical system generates during operation in order to control an electrical parameter (e.g., electrical current, electrical voltage and electrical power at the electrosurgical system's output) and/or a state and/or an operation mode of the electrosurgical system. The type of feedback signal that an electrosurgical system use may change during the operation of the electrosurgical system, for example depending on the electrical current, voltage or power (or any combination thereof) at the output of the electrosurgical system, and/or depending on a current state or operation mode of the electrosurgical system.

Figure 1B:
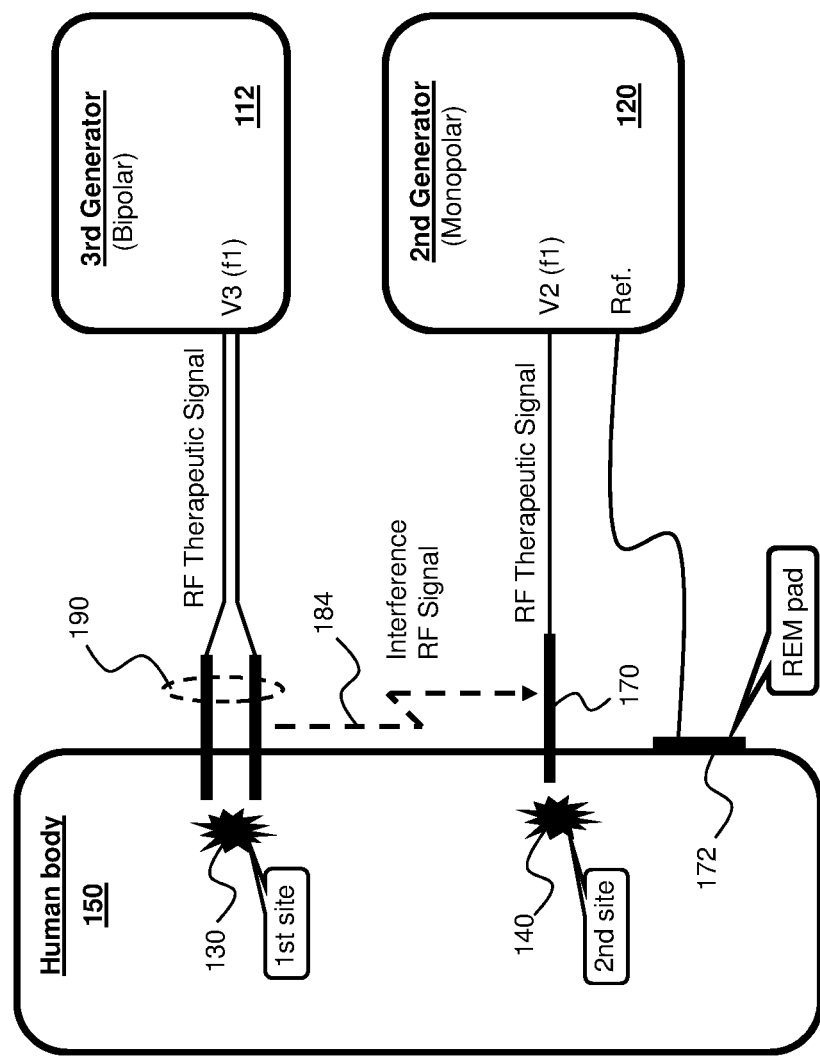

FIGS. 1A and 1B schematically illustrate electrosurgical systems in different electrosurgical treatment setups where operation of one electrosurgical system may interfere with the operation of another electrosurgical system. Referring to FIG. 1A, a first electrosurgical generator 110 and a second electrosurgical generator 120 operate on two separate treatment sites 130 and 140 of a human (or another mammal's) body 150. Treatment sites 130 and 140 may be relatively close (e.g., they may be spaced 10 centimeters away from one another) or far apart from each other (e.g., 1.5 meter away from each other).

Both electrosurgical generator 110 and electrosurgical generator 120 are monopolar electrosurgical systems. Electrosurgical generator 110 includes a treatment electrode 160 via which electrosurgical generator 110 may deliver RF therapeutic signal (V1($f1$)) to treatment site 130, and a REM pad 162. Similarly, electrosurgical generator 120 includes a treatment electrode 170 via which electrosurgical generator 120 may deliver RF therapeutic signal (V2($f1$)) to treatment site 140, and a REM pad 172.

Electrosurgical generator 110 and electrosurgical generator 120 use a continuous feedback signal to continually control their operation, for example to control their output electrical current, or their output electrical voltage, or the power of their output RF therapeutic energy. The value of the feedback signal that is used to control the related electrosurgical system may be relatively small, which may make the feedback signal susceptible ('sensitive') to interferences in the same frequency band.

In some instances (depending; e.g., on the modalities used), the value of the feedback signals in electrosurgical system 110 and 120 may not necessarily be relatively small. However, interference may become an issue when the feedback signal used by, for example, generator 110 is relatively small in relation to the feedback signal that is used by, for example, generator 120, or vice versa. This would occur, for example, if one electrosurgical generator is attempting to deliver a low RF therapeutic power to a body site while the other electrosurgical generator is attempting to deliver a high RF therapeutic power to a different (e.g., nearby) body site.

By way of example, both electrosurgical generators 110 and 120 output therapeutic energy at the same carrier frequency, f1. Therefore, when one electrosurgical generator (for example electrosurgical generator 110) outputs a therapeutic RF signal at frequency f1, the feedback signal (which is produced using current samples, or voltage samples, or both types of samples, of the RF signal, and, therefore, also has the same frequency, f1) that electrosurgical generator 120 (to continue the example) uses to control its own operation is interfered with by the therapeutic RF energy that is output by electrosurgical generator 110. (The RF interference, which is a portion of the RF energy that electrode 160 'transmits' to electrode 170 (due to the electrodes undesirably serving as an RF antenna), is conceptually shown at 180.) RF interference between electrosurgical generator 110 and electrosurgical generator 120 may be mutual; that is, treatment electrode 160 of electrosurgical generator 110 may receive a similar RF interference from treatment electrode 170 when electrosurgical generator 120 outputs therapeutic RF signal via electrode 170. In other words, due to inductive coupling between the electrodes (and the related wires), they act as RF antennae that transmit and receive RF interference signals through air and/or through the body of the subject undergoing the electrosurgical procedure. Another type of interference signal that may detrimentally affect a system's feedback signal may result from stray electrical signals 182 that may travel between the electrodes through the body of the subject undergoing the electrosurgical procedure/treatment.

FIG. 1B shows a two-generator system where electrosurgical generator 110 (a monopolar electrosurgical system) of FIG. 1A is replaced with a bipolar electrosurgical generator 112. Like monopolar electrosurgical generator 110, bipolar electrosurgical generator 112 also outputs therapeutic RF signal (V3($f1$)) via bipolar electrodes 190. Some of the RF energy that bipolar electrosurgical generator 112 outputs as therapeutic RF energy may interfere with the feedback signal, and therefore the operation, of monopolar electrosurgical generator 120. (The RF interference that bipolar electrosurgical generator 112 imposes on electrosurgical generator 120 is conceptually shown at 184.)

RF interference between bipolar electrosurgical generator 112 and electrosurgical generator 120 may be mutual: the RF interference caused by bipolar electrosurgical generator 112 during treatment interferes with the feedback signal that monopolar electrosurgical generator 120 uses for its operation, and the RF interference caused by monopolar electrosurgical generator 120 during treatment interferes with the feedback signal that bipolar electrosurgical generator 112 uses to control its operation.

FIG. 2A shows a plot 200 illustrating an ideal situation in the context of an autobipolar ("ABP") electrosurgical system. The horizontal axis indicates a state/condition of the ABP electrosurgical system; e.g., system's output circuit is closed versus open. The vertical axis conceptually indicates an external output impedance (Z) at the output of the electrosurgical system or at the tip of the electrosurgical device (e.g., at the tip of treatment forceps), though the impedance at these two locations may differ. (The same applies to the axes in FIG. 2B, which is described below.) As described herein, impedance at the output of the electrosurgical system is calculated (estimated) by sampling current and voltage at the output of the electrosurgical system, and if the current and voltage samples are impaired by RF interferences, estimation of the impedance may likely to be unreliable.

When an electrosurgical system performs an electrosurgical procedure, the electrosurgical device (e.g., forceps) delivering treatment may, at times, touch the treated bodily organ or tissue, and at other times it may be intentionally moved away from the treatment site, for example, in order not to provide excess energy to the treated tissue/site, for example in order not to overheat, or otherwise damage, the treated tissue/site. (The treatment delivering device may, at times, be unintentionally moved away from the treatment site.)

In ideal cases, when the treatment device touches the treated tissue (e.g., when the ABP system's electrical circuitry (the electrosurgical system's 'output circuitry', or 'output circuitry' for short) is closed via the tissue), the ABP system would sense a relatively small impedance (Z1, FIG. 2A), which is approximately the impedance of the tissue, and when the treatment device does not touch the treated tissue (i.e., when the ABP system's output circuitry is open), the impedance that the ABP system would sense should theoretically be infinite ($Z_\infty$, FIG. 2A), or, in practice, at least in the order of tens of kilo ohms.

As shown in FIG. 2A, the impedance gap ΔZ1 (FIG. 2A) between Z1 (the impedance in the 'closed circuit' state) and $Z_\infty$ (the impedance in the 'open circuit' state) is very large so that the two distinct impedance states (Z1 and $Z_\infty$) can be distinguished easily. Since the ABP system should stop delivering therapeutic RF energy when the treatment device is moved away from the body, the ability to reliably distinguish between the two impedance states (Z1 and $Z_\infty$) is prerequisite to safe, reliable and efficient operation of the electrosurgical system. However, in practice, the impedance gap is far from being ideal, in part due to the parasitic capacitances existing in the output circuitry of the electrosurgical system (and also in the electrosurgical system itself), as demonstrated in FIG. 2B, which is described below.

FIG. 2B shows a plot 210 illustrating example interference-free situations in the context of an ABP system. When the treatment device (e.g., forceps) touches a treated tissue, see device condition 220; i.e., when the ABP system's output circuitry is closed via the tissue, the ABP system typically senses a relatively small impedance (under line 250) that may change, for example, according to changes in the physiological properties of the tissue, for example, while the tissue is treated. As shown in FIG. 2B, the impedance in the closed circuit state (220) may vary within ΔZ2, which can be within the range of tenths of ohms to kilo ohms, for example.

When the treatment device stops touching the treated site, causing the ABP system's output circuitry to open (system condition 230), the output impedance that the ABP system typically senses in 'open circuit' state 230 is higher than the impedance usually sensed by the ABP system in the 'closed circuit' state (120), but still, it is much lower than desired because of the parasitic impedance imposed on the system's output circuitry by the periphery equipment setting.

Figure 2C:
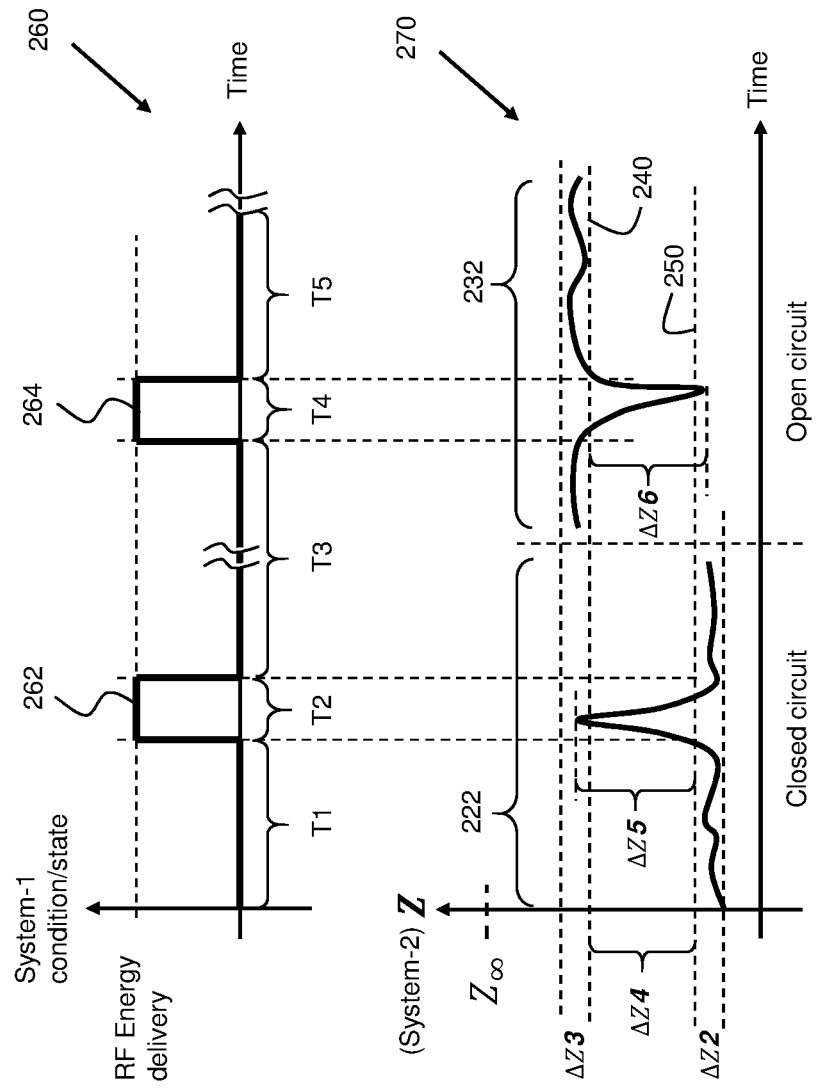
FIG. 2C shows an effect of RF interference on the plot of FIG. 2B.

As shown in FIG. 2B, the impedance variations in the 'open circuit' state (230) can have a magnitude that may be as large as ΔZ3, which can be within the range of hundreds of ohms to tens of kilo ohms. The 'in-between state' impedance gap ΔZ4 between the minimum 'open circuit' impedance (240) and the maximum 'closed circuit' impedance (250) may be, in some systems, 4 kilo ohms, which is much smaller than the ideal impedance gap ΔZ1 (FIG. 2A) (Z1<<ΔZ1; ΔZ1→∞). (Line 250 may represent a value of 2.2 kilo ohms, which is a practical value in some systems.) Because the impedance gap ΔZ4, which is a result of a feedback signal having a certain RF carrier frequency, is relatively narrow, it is susceptible to RF interferences that have the same, or similar, RF frequency. Under certain conditions, using a same, or similar frequency may result in a wrong decision with respect to the state ('open circuit' or 'closed circuit') of the electrosurgical system, as schematically illustrated in FIG. 2C, which is described below.

FIG. 2C shows two plots 260 and 270 that illustrate an impact of an RF interference on a feedback signal in the context of an ABP system that operates in the interrogation mode. Plot 260 shows a system condition/state as a function of time. For example, during time periods T1, T3 and T5 the electrosurgical system does not output RF therapeutic energy, and during time periods T2 and T4 the electrosurgical system outputs RF therapeutic energy, at 262 and at 264. Plot 270 illustrates the effect of the therapeutic RF energy (at 262 and at 264) on an autobipolar electrosurgical system that operates at the same time on another treatment site of a same subject.

When the autobipolar electrosurgical system is at the closed circuit state (at 222), the RF interference shown at 262, being (in this example) a constructive interference, may cause the impedance, which is computed by the autobipolar electrosurgical system by using interfered with voltage and current samples, to be greater than it actually is. (The difference in the value of the impedance caused by the interference is shown as ΔZ5.) As a result of this impedance miscalculation, the value of the impedance may be greater than the minimum value (go above line 240) above which the autobipolar electrosurgical system may stop treatment and, optionally (e.g., depending on the type of electrosurgical system), transition to the interrogation mode. (As a result of this, the autobipolar electrosurgical system may transition from the interrogation mode to the treatment mode even though the electrosurgical forceps do not touch the body of the subject.)

When the autobipolar electrosurgical system is at the open circuit state (at 232), the RF interference shown at 264, being (in this example) a destructive interference, may cause the impedance, which is measured by the autobipolar electrosurgical system, to be lower than it actually is. (The difference in the value of the impedance caused by the interference is shown as $\Delta Z6$.) As a result of this impedance miscalculation, the value of the impedance may be lower than the maximum value (line 250) below which the autobipolar electrosurgical system may transition from the interrogation mode to the treatment mode. (As a result of this, the autobipolar electrosurgical system may transition from the treatment mode to the interrogation mode even though the electrosurgical forceps touch the body of the subject.)

Figure 3:
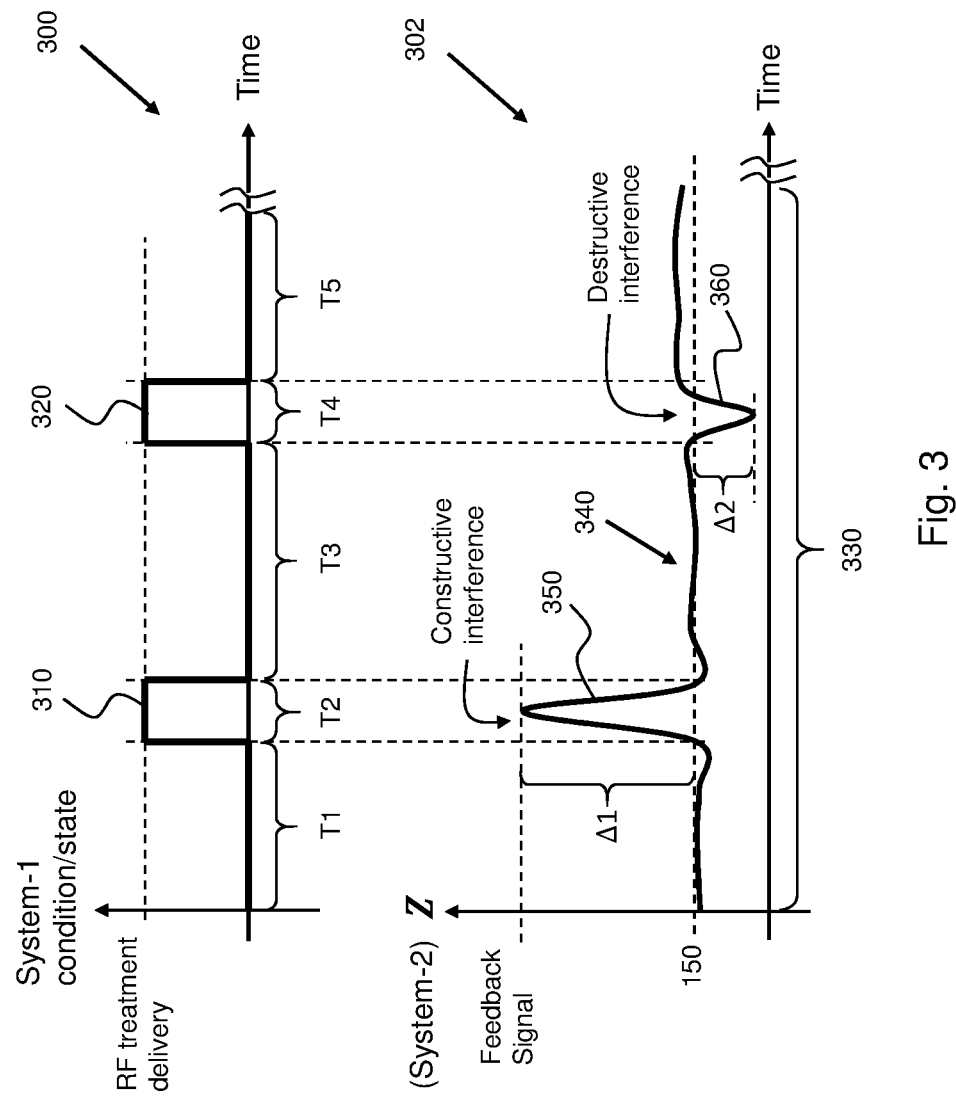
FIG. 3 shows an effect of an RF interference on a feedback signal that an electrosurgical system uses to control its state and/or output electrical parameter.

When the autobipolar electrosurgical system is in the treatment mode, it continues to sample voltage and current at the output of the electrosurgical system, and to produce, from either voltage samples or current samples or from both types of samples, a feedback signal to control the system's output current, voltage or power, or system's state or operation mode. Depending on the state or operation mode of the electrosurgical system, it may use voltage and current samples to compute (evaluate) the output impedance of the electrosurgical system, and use the computed impedance (solely or in combination with current samples and/or voltage samples) to control the state of the electrosurgical system and/or the system's output current, voltage or power FIG. 3 shows two plots 300 and 302 that illustrate an effect of an RF interference on a feedback signal in a general case. (These plots may be applicable to all types of electrosurgical systems.) Plot 300 shows a system condition/state of a first electrosurgical system (designated as "System-1" in FIG. 3) as a function of time. For example, during time periods T1, T3 and T5 System-1 does not output RF therapeutic energy, and during time periods T2 and T4 System-1 outputs RF therapeutic energy, at 310 and at 320, at some carrier frequency. Plot 302 illustrates the effect of the RF therapeutic energy (at 310 and at 320) on the feedback signal of a second electrosurgical system (designated as "System-2" in FIG. 3) that operates at the same time on another site of a same subject, and using the same, or similar, carrier frequency as System-1. (Each of System-1 and System-2 can be any type of electrosurgical system.)

Assume that during time period 330 System-2 is in the treatment mode of operation. During time period 330, System-2 may use a continuous feedback signal 340 to continually control the system's output electrical current, voltage or output power, and, if the system is an autobipolar electrosurgical system, also to determine whether the system is to transition from the treatment mode to the interrogation mode. The feedback signal may be derived (e.g., computed) from current samples and/or voltage samples that are continuously read to reflect the electrical condition or state of the electrosurgical system at any time.

Being (in this example) a constructive interference, RF interference 310 may increase the value of feedback signal 340, as shown at 350. Being (in this example) a destructive interference, RF interference 320 decreases the value of feedback signal 340, as shown at 360. The extent of the increase ($\Delta 1$ in FIG. 3) and the decrease ($\Delta 2$ in FIG. 3) in the value of feedback signal 340 depend, among other things, on the intensity of the RF interference. Since the electrosurgical system affected by the RF interference makes operational decisions based on the value of the feedback signal, which may be produced from interfered with current samples and/or interfered with voltage samples, it may take a wrong decision due to its incorrect value. For example, System-2 (the electrosurgical system experiencing RF interference in FIG. 3) may determine to control its output electrical current instead of controlling its output voltage, or (in another example) to control its output therapeutic RF energy instead of controlling its output voltage, or (in another example) System-2 may inefficiently control an electrical parameter (e.g., its output electrical current, voltage or power), etc.

Figure 4:
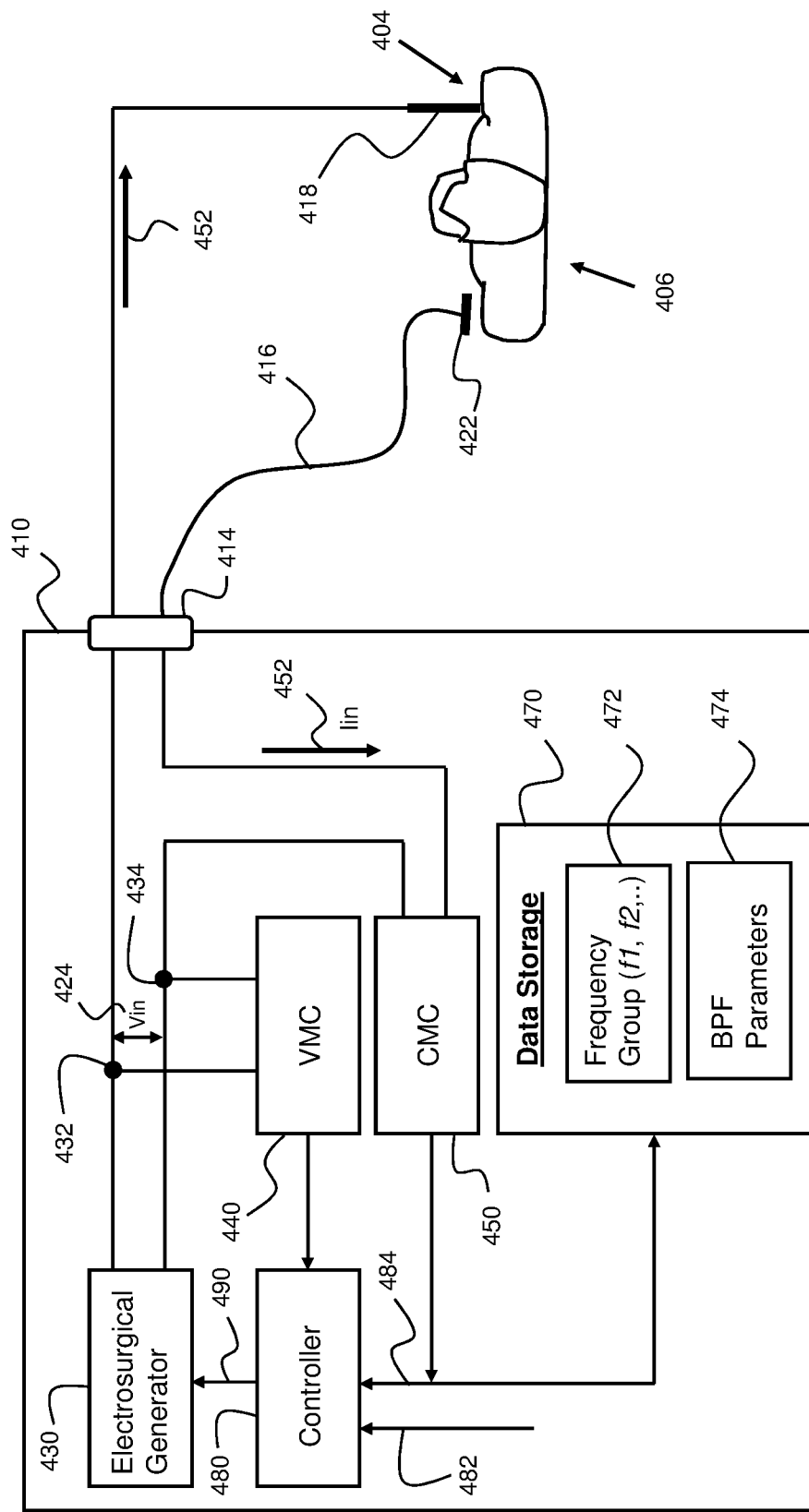
FIG. 4 shows a block diagram of an electrosurgical system according to an example embodiment.

FIG. 4 is a block diagram of an electrosurgical system 410. Electrosurgical unit 410 may include an electrosurgical generator 430 (e.g., an RF signal/energy generator), a voltage monitoring circuit ("VMC") 440, a current monitoring circuit ("CMC") 450, a data storage 470 and a controller 480 to control operation of electrosurgical generator 430. Electrosurgical system 410 may also include a connector or adapter 414 via which electrosurgical generator 430 outputs therapeutic RF energy and, depending on the type of electrosurgical system, also interrogation signal/energy. In general, controller 480 may control an electrical parameter of electrosurgical system 410 (e.g., output current, voltage or power), and it may also control the state of operation mode of electrosurgical system 410.

If electrosurgical system 410 is an autobipolar system, electrosurgical generator 430 may, at times, generate low energy RF interrogation signal, for example less than 1 watt, for example at a 'carrier' frequency within the range 300 KHZ-500 KHz, for example, during an impedance monitoring/interrogation phase (by using an interrogation mode of the system). Electrosurgical generator 430 may also generate high energy (e.g., 1-70 watt) therapeutic RF signal that electrosurgical system 410 may deliver, during an electrosurgical procedure (in a treatment mode of operation), to a bodily organ or tissue site (e.g., electrosurgical site 404) of a subject 406.

An electrosurgical generator may use a same frequency for both outputting therapeutic RF energy and for generating a feedback signal, or it may use separate frequencies for these functions, as described below in more detail:

1. A monopolar electrosurgical generator may be interfered with by another electrosurgical generator if it uses the same (or a too close) frequency as the interfering electrosurgical generator. In this scenario, the RF frequency of the feedback signal and the RF frequency of the output RF signal of the interfered with generator are the same, because the feedback signal is sampled 'out' (e.g., derived from) from the system's output RF signal.

2. In an autobipolar electrosurgical generator, however, impedance interrogation signal is not sampled/derived from therapeutic RF energy, but, rather, is generated between therapeutic RF energy activations ('bursts'). Therefore, the frequency of the impedance interrogation signal and the frequency of generator's output RF signal can differ. In such a case, the autobipolar generator might be interfered with if the interfering generator outputs an RF energy whose frequency is identical, or too close, to the frequency of the impedance interrogation signal. (The interfered with generator may use a different frequency to output RF therapeutic energy.)

Electrosurgical system 410 may deliver the therapeutic RF energy that electrosurgical generator 430 generates to site 404 via an electrosurgical device, which, in the case of a monopolar system, includes one electrode 418 and a REM pad 422. In the case that the electrosurgical device is a bipolar system, the electrosurgical device may include a pair of two electrode tines. (The electrosurgical device is a device delivering therapeutic RF energy from the electrosurgical system to the treated site in order to perform various surgical operations, for example coagulation, ablation, cutting and/or other operations.)

Controller 480 may receive (e.g., from a user; e.g., from a surgeon operating the system), for example by using a hand switch or a foot switch, an input signal or a message 482 instructing controller 480 to transition electrosurgical system 410 to the treatment mode in which electrosurgical generator 430 generates therapeutic (high power) RF energy, or to stop generating therapeutic RF energy. Alternatively, this function may be performed automatically by controller 480, which may control operation of a monopolar electrosurgical system or a bipolar electrosurgical system. For example, controller 480 may determine when an operation mode of the electrosurgical system should be activated (transitioned to), deactivated, resumed, etc. based on a feedback signal, which reflects, represents, is related to or derived (e.g., sampled) from the output RF energy, that controller 480 may receive, for example, from VMC 440, or from CMC 450, or from both current and voltage monitoring/sampling circuits 440 and 450. (In case a control scheme relies on the electrosurgical system's output impedance, the feedback signal may include, or may take into account or factor in, both electrical current samples and electrical voltage samples.) The feedback signal may reflect, represent, be related to or be derived from voltage Vin (shown at 424) that VMC 440 samples between points 432 and 434, or reflect, represent, be related to or derived from the system's output current 452 that CMC 450 samples, or correspond to or reflect, represent, be related to or derived from both voltage samples and current samples which are respectively sampled by VMC 440 and CMC 450.

Controller 480 may receive, from VMC 440 and/or from CMC 450, signal(s), voltage samples and/or current samples, or data that represent the feedback signal. Alternatively, control 480 may receive digitized voltage samples and/or digitized current samples from VMC 440 and/or from CMC 450, and use the digitized samples to produce a feedback signal in order to effect any of the control schemes described herein. Another type of information that an electrosurgical system may use may be obtained (e.g., computed) from the output of multiple BPFs (Goertzel filters), to independently filter voltage samples and current samples at specific frequencies, for example at the candidate frequencies of frequency group 472. Regardless of the electrical parameter (current, voltage or power) that controller 480 controls, controlling the electrical parameter is improved (e.g., is made more accurate relative to a conventional electrosurgical system) because controller 480, selects for electrosurgical generator 430, a frequency that, among the candidate frequencies, is the least susceptible to (including minimal) RF interferences.

Controller 480 may, at times, temporarily activate an interference sensing mode in which controller 480 may sense RF interferences in each frequency in the group of candidate frequencies, and select for the electrosurgical generator 430 a currently quiet, or the quietest, frequency among the candidate frequencies. Controller 480 may transition to the interference sensing mode according to an interference sensing interval in order to select the quiet, or the quietest, frequency for the electrosurgical generator. For example, controller 480 may transition to the interference sensing mode (i.e., transition to the interference sensing mode) once every n1 seconds (e.g., n1=20 seconds, n1 may have other values), or once every n2 minutes (e.g., n2=5 minutes, n2 may have other values). (Other interference sensing intervals may be selected.)

In case electrosurgical system 410 is an autobipolar electrosurgical system controller 480 may calculate, during an impedance interrogation phase, the system's instantaneous output impedance, Zout, by applying an interrogation voltage, Vin, 424, and measuring that voltage by VMC 440, and by concurrently measuring the resulting interrogation current Iin (452) by CMC 450. Controller 480 may compute the output impedance Zout (Zout=Vin/Iin) and, based on the value of Zout, determine the next operation mode or state of electrosurgical system 410. 'Knowing' the output voltage (Vout) and output current (Tout) at treatment electrode 418, controller 480 may also determine (and control) the therapeutic RF energy actually provided to the treated site when the electrosurgical system operates in the treatment mode. Knowing the actual therapeutic RF energy delivered to the treated site, controller 480 may control (490) the operation (e.g., an output electrical parameter) of electrosurgical generator 430 to deliver an optimal amount of therapeutic energy to the treated site at any given time during treatment. When electrosurgical generator 430 is not delivering therapeutic RF energy, it may deliver (in an autobipolar electrosurgical system), at times, a relatively small average interrogation current 452 (e.g., in the order of micro amps), for example which is in compliance with IEC safety regulations, to interrogate (sense, evaluate) the magnitude of a tissue impedance.

VMC 440 may include an isolation transformer that acts as an inductive pickup device. The transformer primary side may be electrically connected between lead points 432 and 434 for inducing a voltage signal on the transformer's secondary windings in response to the RF energy that electrosurgical generator 430 outputs through these points. VMC 450 (a current sensing circuit) senses, as feedback, an electrical current returning to electrosurgical system 410 as a result of the RF energy that electrosurgical generator 430 outputs. Being sampled, or derived, from RF energy that the electrosurgical system outputs, voltage signal 424 and current signal 452 are alternating current (AC) signals that (when in the treatment mode) represent the therapeutic RF energy that electrosurgical generator 430 outputs to the electrosurgical device in order to control an electrical parameter (e.g., current, voltage, power) of the therapeutic RF energy, or (in the case of an autobipolar electrosurgical system operating in the interrogation mode), that may be used to evaluate the output impedance of the electrosurgical system in order to determine, for example, whether the electrosurgical system is to transition from the interrogation mode to the treatment (therapeutic RF energy delivering) mode.

In a bipolar configuration, the electrosurgical device includes two electrodes (not shown), which are used at a surgical site of the patient with one electrode providing the return path for the output of electrosurgical generator 430. In a monopolar configuration, the electrosurgical device includes one electrode 418 while another electrode (422) is connected to a surface near the patient and provides the return path. Although monopolar and bipolar configurations are used in electrosurgical systems, they are electrically equivalent and equally suited for use with the control methods and control system of the present disclosure.

In data storage 470 may be stored first data that represent a group, or list, of candidate frequencies (f1, f2, f3, ...), and second data that represent parameters (e.g., center frequency, filter width) and/or coefficients that define a configurable band pass filter (BPF) and enable (e.g., controller 480) to configure the BPF to selectively pass any frequency in the frequency group, according to need.

The RF energy that the electrosurgical system outputs (for therapy or for impedance interrogation) is sampled (e.g., by VMC 440 and CMC 450) at a sampling frequency. Knowing in advance the frequency that an electrosurgical system is going to use to deliver therapeutic RF energy which, if ignored, may interfere with the operation of the electrosurgical system subject of the invention, and also knowing the sampling frequency that the electrosurgical system subject of the invention is to use to sample its own RF energy, enable to select candidate frequencies among which one candidate frequency may be selected as an operational frequency for the electrosurgical system. To this effect, each candidate frequency in the group of candidate frequencies may be selected (as potential electrosurgical system's carrier frequency, or, in some embodiments, as potential frequencies for a feedback signal) if it satisfies a sampling condition known in the field of digital filters as the coherent sampling condition, which is given below:

$$\frac{f_{in}}{f_s} = \frac{M_{cycles}}{N_{samples}}$$

where fin is a frequency of the RF energy (hence of the feedback signal), fs is a sampling frequency at which the electrosurgical system's output voltage and/or output current (from which the feedback signal is produced) is sampled (e.g., by VMC 440 and CMC 450, respectively), Mcycles is the number of signal periods/cycles in a sampled set (in a sampling window), and Nsamples is the number of samples in the sampled set (in the sampling window).

In an aspect of the invention, controller 480 may be configured to, among other things, activate the interference sensing mode of operation, which may include refraining (e.g., causing the electrosurgical generator to refrain) from outputting RF energy and, while it refrains from outputting RF energy, and measuring an RF interference for each frequency in the group of candidate frequencies. To this effect, controller 480 may use information stored in data storage 470 (e.g., BPF configuration parameters and/or coefficients 474) to configure a BPF to selectively pass signals having only the candidate frequencies, to thus measure interference for each candidate frequency. Then, controller 480 may select a particular frequency from the group of candidate frequencies for which the measured RF interference is below a predetermined threshold, or the lowest, and output RF energy at the selected frequency. Controller 480 may control the operation of the electrosurgical system by using a feedback signal which is derived from the output RF energy and, like the output RF energy, has the same selected frequency. To this effect, controller 480 may configure the BPF to pass only the particular frequency that controller 480 selects for the electrosurgical system, and to reject (cancel out) the interfering RF signal(s). In this case, the frequency of the feedback signal is the same as the frequency of the system's output RF energy. However, if an electrosurgical system uses different frequencies for the feedback signal and output RF energy, controller 480 may assign the quiet frequency (or the lowest interfered with frequency) to the feedback signal in order for the feedback signal to be reliable, and configure the BPF to pass only the feedback signal, and to reject (cancel out) the interfering RF signal(s).

In another aspect of the invention, controller 480 may be configured, among other things, to refrain from outputting RF energy and to measure an RF interference for each frequency in the group of frequencies. Controller 480 may be also configured to select, for a feedback signal (a signal used to control the operation of the electrosurgical system), a frequency from the group of candidate frequencies for which the measured RF interference is below a predetermined threshold, or the lowest, and to control operation of the electrosurgical system by using the feedback signal whose frequency is the selected frequency. By selecting an operational (carrier) frequency for, or a frequency for a feedback signal to be used by, the electrosurgical system in the way described herein, the interference problem that is described herein is mitigated.

In some embodiments, controller 480 may use the Goertzel filter as a BPF to process the voltage samples and the current samples. Measuring interferences in the frequencies of the frequency group can be done by using any kind of BPF, and measuring the feedback signal may beneficially be done by using the Goertzel filter as a BPF.

In general, the BPF (e.g., a Goertzel filer) may be used in two phases or ways:

(1) Sensing interferences—To sense RF interference in each RF frequency in the group of candidate frequencies in order to identify a quiet, or the quietest, RF frequency, and, after the quiet, or quietest, RF frequency is identified, to use this frequency as the electrosurgical system's feedback (control) signal and/or as the electrosurgical system's RF carrier frequency (for outputting therapeutic RF energy and/or interrogation (RF) signals.

(2) Control—After controller 480 selects the quietest RF frequency from the frequency group, and while using the selected frequency, controller 480 may use the BPF to accurately (with interferences essentially eliminated or significantly diminished) measure a feedback signal that originates (e.g., derived, or otherwise obtained) from, or represents (2.1) Therapeutic RF energy that is output by an electrosurgical system in order to control an electrical parameter of the therapeutic RF energy that the electrosurgical system outputs. In some cases an electrosurgical system may use a feedback signal that originates from the therapeutic RF energy (in the treatment mode) to determine whether the electrosurgical system is to transition from one state to another, or from the treatment mode to an interrogation mode.

(2.2) Non-therapeutic energy that is output by an electrosurgical system, for example in the interrogation mode, in order to, for example, evaluate the system's output impedance in order to determine whether, or when, the electrosurgical system is to transition, for example, from the interrogation mode to the treatment mode.

In some embodiments, an electrosurgical system similar to electrosurgical system 410 may include an electrosurgical generator similar to electrosurgical generator 430, and a controller similar to controller 480, and the controller may be configured to cause the electrosurgical generator to refrain from outputting RF energy, to measure an RF interference for each frequency in a group of candidate frequencies when the electrosurgical generator refrains from outputting RF energy, to select a frequency from the group of candidate frequencies for which the measured RF interference is below a predetermined threshold, or the lowest, and to control operation of the electrosurgical system by using a feedback signal having a frequency which is set to the selected frequency. The feedback signal may be derived from an RF energy that is output by the electrosurgical generator. For example, the RF energy may be therapeutic RF energy that the electrosurgical system outputs when it operates at a treatment mode, or an interrogation signal that the electrosurgical system outputs in order to determine, for example, transitions between interrogation mode and treatment mode.

Carrier frequencies for electrosurgical systems typically range from 300 KHz to 500 KHz, but some of these frequencies may be outside those bounds under certain circumstances. For a particular sample rate under the assumption of coherent sampling, the number of samples per signal period determines the possible carrier frequencies. For example, for a sampling frequency of 20 million samples per second, the possible carrier frequency is computed by dividing the sample rate (frequency) by the number of samples per one signal period. For example, 40 samples per signal period equates to (result in) a carrier frequency of 500 KHz; 50 samples per signal period equates to a carrier frequency of 400 KHz, and 60 samples per signal period equates to a carrier frequency of 333.33 KHz. Therefore, over 20 possible carrier (candidate) frequencies satisfy the coherent sampling condition for the 20 million samples/second application between 300 KHz and 500 KHz.

FIG. 5 shows a method for mitigating RF interferences during operation of an electrosurgical system according to an example embodiment. FIG. 5 is described in association with FIG. 4. At step 510, controller 480 may transition electrosurgical system 410 to an interference sensing mode in which controller 480 may refrain from outputting RF energy and, while refraining from outputting RF energy, controller 480 may measure RF interferences in any candidate frequency in a group of candidate frequencies (472) that may be stored/listed, for example, in data storage 470. Controller 480 may use REM pad 422 as an RF antenna to sense RF interferences in the candidate frequencies one candidate frequency at a time (e.g., one after another), or controller 480 may sense RF interferences in all the candidate frequencies at the same time. Controller 480 may alternatively measure RF interferences using a dedicated RF antenna. (A dedicated antenna, or sensor, may be mounted, or be part of, for example, REM pad 422.) Controller 480 may store (for example in data storage 470) a value indicating or representing an intensity of a measured RF interference for each candidate frequency, for example, for comparison purpose.

At step 520, controller 480 may identify and select a candidate frequency from the group of candidate frequencies for which the measured RF interference is below a predetermined threshold, or the lowest, and cause electrosurgical generator 430 to generate RF energy at the selected candidate frequency. The type of RF energy that controller 480 causes electrosurgical generator 430 to generate at the selected candidate frequency may depend on the state electrosurgical system 410 is currently in, or on the operation mode actually used by electrosurgical system 410, which may be of any type (e.g., bipolar, monopolar, autobipolar). (Electrode 418 and REM pad 422 are shown for a monopolar electrosurgical system. However, electrosurgical system 410 may be bipolar (or autobipolar) electrosurgical system and the electrodes delivering therapeutic RF energy may change accordingly.)

Regardless of the type of RF energy (therapeutic energy or interrogation energy) that the electrosurgical generator 430 generates, VMC 440 and CMC 450 may respectively sample the electrosurgical system's output voltage and current and produce, from these samples, a feedback signal for controller 480. Alternatively, VMC 440 and CMC 450 may transfer to controller 480 signals, voltage and current samples, or data, and controller 480 may use these samples, or some of them, to produce the feedback signal required to control operation of the system, or part of the system. At step 530, controller 480 controls the operation of electrosurgical system 410 by using the feedback signal that was sampled from the generated RF energy.

Controller 480 may repeat (540) steps 510 through 530, for example according to a predetermined schedule (e.g., according to an interference sensing interval), in order to ensure that the feedback signal produced from the voltage and/or current samples respectively obtained by VMC 440 and CMC 450 is reliable (i.e., not interfered with, for example, by an electrosurgical generator of another; e.g., nearby, electrosurgical system) throughout the entire, or at least during most of the, electrosurgical procedure.

FIG. 5 refers to embodiments in which the frequency of the feedback signal and the frequency of the output therapeutic RF energy are identical, and controller 480 assigns the quiet, or quietest, frequency to the electrosurgical system to enable it to produce the two types of signals. FIG. 6, which is described below, refers to embodiments in which the frequency of the feedback signal and the frequency of the output RF energy are different, and controller 480 assigns the quiet, or quietest, frequency to the feedback signal (but not to the therapeutic RF energy) or, more specifically, to an electric circuit that outputs RF energy from which the feedback signal is derived.

FIG. 6 shows a method for mitigating RF interferences during operation of an electrosurgical system according to another example embodiment. FIG. 6 is described in association with FIG. 4. At step 610, controller 480 may transition electrosurgical system 410 to an interference sensing mode in which controller 480 may refrain from outputting RF energy, and, while refraining from outputting RF energy, measure RF interferences in each candidate frequency in a group of candidate (RF) frequencies that may be stored (e.g., as a list, as a binary code, etc.), for example, in data storage 470. Controller 480 may sense RF interferences in each particular candidate frequency, for example, by setting a fundamental frequency of a BPF to the particular candidate frequency, and measuring the filter's output at that RF frequency. At step 620, controller 480 may identify and select a candidate (RF) frequency from the group of candidate (RF) frequencies for which the measured RF interference is below a predetermined threshold, or the lowest.

At step 630, controller 480 may operate electrosurgical system 410 using the selected RF frequency. Operating electrosurgical system 410 by controller 480 by using the selected RF frequency may include producing a feedback signal at the selected frequency, and controlling operation of the electrosurgical system by using the feedback signal. Controller 480 may derive the feedback signal from a therapeutic RF energy that is output by the electrosurgical generator when the electrosurgical system operates at a treatment mode, or from an interrogation signal that is generated by the electrosurgical system before the electrosurgical system transitions between an interrogation mode and the treatment mode. Controller 480 may use the feedback signal to calculate an impedance, Z, at the output of the electrosurgical system, and control the operation of the electrosurgical system by using the calculated impedance, Z. A therapeutic RF energy and a feedback signal may have, in some embodiments, a same frequency, and, in other embodiments, they may have different frequencies, with the feedback signal having the selected (RF) frequency.

Controlling the operation of electrosurgical system 410 by controller 480 may include controlling an output electrical current and/or an output electrical voltage of electrosurgical system 410 and/or an electrical power of the RF energy, and/or transitioning electrosurgical system 410 between an interrogation mode of operation, in which it outputs an interrogation signal, and a treatment mode, in which the electrosurgical system may output therapeutic RF energy.

Controller 480 may repeat (640) steps 610 through 630, for example according to a predetermined schedule (e.g., according to an interference sensing interval), in order to ensure that the feedback signal produced from the voltage and current samples respectively obtained by VMC 440 and CMC 450 is reliable (i.e., not interfered with, for example, by an electrosurgical generator of another; e.g., nearby, electrosurgical system) throughout the entire electrosurgical procedure.

FIG. 7 shows a method for mitigating RF interferences in, and during operation of, an electrosurgical system according to another example embodiment. FIG. 7 is described in association with FIG. 4. At step 710, controller 480 may transition electrosurgical system 410 to an interference sensing mode in which controller 480 may refrain from outputting RF energy, and, while refraining from outputting RF energy, measure RF interferences in any candidate frequency in a group of candidate frequencies that may be listed 472, for example, in data storage 470. Controller 480 may use electrode 418, or a dedicated RF antenna, to sense RF interferences in the candidate frequencies. Controller 480 may store (for example in data storage 470) a value indicating an intensity of a measured RF interference for each candidate frequency, for example, for comparison purpose.

At step 720, controller 480 may identify and select a candidate frequency from the group of candidate frequencies for which the measured RF interference is below a threshold value, or the lowest. Controller 480 may, then, cause electrosurgical generator 430 to output RF energy at the selected frequency. As described herein, the RF energy that controller 480 may cause electrosurgical generator 430 to output may be high RF energy (for therapeutic use), or low RF energy (e.g., for impedance interrogation use when the related electrosurgical system is in the interrogation mode). Controller 480 may use the system's output impedance to control a transitioning of the electrosurgical system from one state or operation mode to another, or to control an electrical parameter of the RF energy that the electrosurgical system outputs, for example during treatment. (As described herein, the system's output impedance is calculated from current and voltage samples that may be obtained (e.g., derived), for example, by VMC 440 and CMC 450, from the system's output RF energy.)

At step 730, controller 480 may compute the electrosurgical system's output impedance, Z, by using current and voltage samples of the output RF energy, and, at step 740, controller 480 may control operation of the electrosurgical system based on the compute impedance, Z. Controlling operation of the electrosurgical system based on the compute impedance, Z, may be performed as described herein. For example, if the impedance at the system's output is relatively low (e.g., lower than a threshold impedance value), controller 480 may control the system to a current limit, and if the impedance is relatively high (e.g., higher than a threshold impedance value), controller 480 may control the system to a voltage limit, and if the impedance is in a middle of the impedance range (e.g., between these two impedance thresholds) for the active modality, controller 480 may control the system's output power.

Controller 480 may repeat (750) steps 710 through 740, for example according to a predetermined schedule, in order to ensure that the feedback signal derived from the voltage and current samples, which is the basis for the control schemes described herein, is reliable throughout the entire electrosurgical procedure.

In connection with the methods described herein, for example in connection with FIGS. 5-7, controlling operation of the electrosurgical system (for example by controller 480, FIG. 4) may include, for example, calculating by controller 480, from or using the feedback signal, a value of an operational parameter of the electrosurgical system, and controlling, by controller 480, the operation of the electrosurgical system based on the calculated value of the operational parameter. The calculated operational parameter may be, for example, an impedance (Z) measured at the output of the electrosurgical system, an RF energy power that the electrosurgical system outputs, etc. Controller 480 may control the operation of the electrosurgical system based on the calculated impedance, Z, for example by controlling an output electric current (I) of the electrosurgical system, or an output electric voltage (V) of the electrosurgical system site, or an electrical power (P) of the RF energy that is output by the electrosurgical generator 430.

Controlling the operation of the electrosurgical system (e.g., electrosurgical system 410) may include, for example, setting the BPF's fundamental, or main, frequency to the selected frequency, and filtering the feedback signal by the BPF whose fundamental, or main, frequency has been set to the selected frequency.

FIG. 8 shows a frequency magnitude response graph 800 of a digital BPF according to an example embodiment. The frequency magnitude response of the BPF is equivalent to the $\sin(x)/x$ (sinc function) like magnitude response of a single bin of an N-point DFT, a portion of which is shown in FIG. 8. Using a BPF, if implemented as a Goertzel filter, enables to detect the presence of a single continuous-wave sinusoidal tone in a simple way, yet efficiently, and to effectively isolate a frequency of interest ('tone')—in our case individual candidate frequencies—for the purpose of detecting RF interferences, and, during operation, to cancel out interferences whose frequency is different than the filter's main/primary frequency. Therefore, using a Goertzel filter as the BPF facilitates the selection of a quiet, or the quietest, carrier frequency for an electrosurgical generator, and, in particular, for the purpose of obtaining an interference-free feedback signal which is prerequisite to accurate and reliable control of any electrosurgical system.

Referring again to FIG. 8, assume that frequency magnitude response curve 810 is a frequency magnitude response curve of an interfering electrosurgical system whose carrier frequency is f1 (e.g., f1=434,028 KHz). The magnitude (in db) of frequency magnitude response curve 810 spans between db(min) and db(max). Each point of frequency magnitude response curve 810 that has magnitude db(min) is a 'null point' of the frequency magnitude response curve.

If two electrosurgical systems operate at a same carrier frequency f1, one electrosurgical system may interfere with the operation of the other electrosurgical system because of the constructive, or destructive, effect of the therapeutic RF energy of one electrosurgical system on the feedback signal that the other electrosurgical system uses to control its operation. If the carrier frequency of the interfered with electrosurgical system is arbitrarily changed to, say, f11, or to f51, (that is, to a non-null point), the interference problem may still exist because of the RF energy spill-over of the interfering RF energy (which is generated using carrier frequency f1) to other frequencies. In other words, not every frequency that differs from the interfering frequency, f1, can solve the interference problem because energy of the interfering signal, at frequency f1, spills-over to 'neighboring' frequencies, though this effect gradually decreases. However, every null frequency ('null frequency'—a frequency that is located at, or coincides with, a null point in the frequency magnitude response graph) may solve the problem because the energy spilled-over due to the interference is largely attenuated (e.g., to db(min), FIG. 8) at the null points/frequencies. Therefore, if the interfered with electrosurgical system selects a null frequency as its operational carrier frequency, the feedback signal used by the electrosurgical system to control its operation is, to a large degree, free of interference. If the feedback signal, which represents, or is derived from, the current and/or voltage samples discussed herein, is interference free, the electrosurgical system's parameter that is controlled (e.g., the electrosurgical generator's output voltage and/or current and/or electrical power) can be calculated accurately and reliably.

Referring again to FIG. 8, example null points of the filter are shown at 'null' frequencies f2, f3, f4 and f5. (The number of null frequencies from which the interfered with electrosurgical system may select a candidate frequency as its carrier/operational frequency, or as a frequency of the feedback signal, may be less than four, or greater than four.) The second electrosurgical system may use any of the candidate null frequencies f2, f3, f4 and f5 as its carrier frequency. However, it would be beneficial for the interfered with electrosurgical system to identify one of the null frequencies which is a quiet, or the quietest, frequency (e.g., a frequency which is the least interfered with by RF interference).

By way of example, the interfering frequency, f1, may be equal to 434,028 Hz, and the null (candidate) frequencies may have the following values: f2=416,662 Hz, f3=425,120 Hz, f4=443,262 Hz, and f5=452,899 Hz. In general, the locations of the null points on the frequency axis of the frequency magnitude response graph are a result of the signal's sampling frequency, and also a result of these frequencies satisfying the coherent sampling condition, so the signal's sampling frequency, and other factors, may conveniently be set or chosen such that the candidate frequencies can be located at desired null locations on the frequency axis.

In some embodiments, when the candidate frequencies are known (e.g., calculated in advance; e.g., based on coherent sampling, sampling frequency, etc.) and stored in, for example, data storage 470 (FIG. 4), the controller (e.g., controller 480) controlling the electrosurgical generator (e.g., electrosurgical generator 430) may initially operate the electrosurgical generator using a default RF carrier frequency that may be included in the group of candidate frequencies. If an RF interference is detected in the default RF carrier frequency, the electrosurgical generator may 'scan' the list of available candidate frequencies in the frequency group for the (maybe a different) "quietest" frequency, and replace the electrosurgical generator's interfered with RF carrier frequency with the quiet, or quieter, RF frequency.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Embodiments of the invention may include a computer or processor non-transitory storage medium, such as for example a memory, a disk drive, or a USB flash memory, encoding, including or storing instructions, e.g., computer-executable instructions, which when executed by a processor or controller, carry out methods disclosed herein. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of electrosurgical systems (e.g., bipolar type electrosurgical systems, autobipolar type electrosurgical systems, monopolar type electrosurgical systems, and the like) and to various types of electrosurgical devices. Hence the scope of the claims that follow is not limited by the disclosure herein to any particular electrosurgical system or electrosurgical device.

The invention claimed is:

1. A method of mitigating interferences during operation of an electrosurgical system, comprising:
    by an electrosurgical system configured to output a therapeutic radio frequency ("RF") energy, performing,
        refraining from outputting RF energy;
        measuring, while refraining from outputting RF energy, an RF interference for a group of candidate frequencies;
        selecting, from the group of candidate frequencies, a frequency for which the measured RF interference is below a predetermined threshold and generating RF energy at the selected frequency; and
        controlling operation of the electrosurgical system by using a feedback signal sampled from the generated RF energy.

2. The method as in claim 1, wherein controlling the operation of the electro surgical system comprises:
    calculating, using the feedback signal, a value of an operational parameter of the electrosurgical system; and
    controlling the operation of the electrosurgical system based on the calculated value of the operational parameter.

3. The method as in claim 2, wherein the calculated operational parameter is an impedance (Z) at the output of the electrosurgical system.

4. The method as in claim 2, wherein controlling the operation of the electrosurgical system comprises controlling an output electric current (I) of the electrosurgical system, or an output electric voltage (V) of the electrosurgical system site, or an electrical power (P) of the RF energy that is output by the electrosurgical system, or determining a state or an operational mode of the electrosurgical system.

5. The method as in claim 1, wherein the electrosurgical system is selected from the group consisting of: monopolar electrosurgical system, bipolar electrosurgical system and autobipolar electrosurgical system, and wherein each of the monopolar electrosurgical system, bipolar electrosurgical system and autobipolar electrosurgical system is configured to produce the feedback signal at the selected frequency.

6. The method as in claim 5, wherein the feedback signal is derived from therapeutic RF energy that the electrosurgical system outputs.

7. The method as in claim 5, wherein the feedback signal is derived from an interrogation signal generated by the electrosurgical system.

8. The method as in claim 1, wherein measuring an RF interference for each particular frequency in the group of candidate frequencies comprises configuring a band pass filter to pass only the particular frequency.

9. The method as in claim 8, wherein the band pass filter is a Goertzel filter.

10. The method as in claim 8, wherein each candidate frequency satisfies the coherent sampling condition:

$$\frac{f_{in}}{f_s} = \frac{M_{cycles}}{N_{samples}}$$

where fin is a frequency of the output RF energy, fs is a sampling frequency, Mcycles is the number of cycles in a sample set or in a sample window, and Nsamples is the number of samples in the sample set or in the sample window.

11. The method as in claim 8, wherein controlling the operation of the electro surgical system comprises setting a frequency of the band pass filter to the selected frequency and filtering the feedback signal by the band pass filter at the selected frequency.

12. An electrosurgical system comprising:
an electrosurgical generator to output therapeutic radio frequency ("RF") energy; and
a controller to control operation of the electrosurgical generator;
wherein the controller is configured to,
cause said electrosurgical generator to refrain from outputting RF energy;
measure an RF interference for each frequency in a group of candidate frequencies when the electrosurgical generator refrains from outputting RF energy;
select a frequency from the group of candidate frequencies for which the measured RF interference is below a predetermined threshold; and
control operation of the electrosurgical system, the control comprising using a feedback signal having the selected frequency.

13. The electrosurgical system as in claim 12, wherein the controller is configured to derive the feedback signal from RF energy that the electrosurgical generator outputs.

14. The electrosurgical system as in claim 12, wherein each frequency in the group of candidate frequencies coincides with a null point of a magnitude-frequency response curve of a band pass filter.

15. The electrosurgical system as in claim 14, wherein the band pass filter is a Goertzel filter.

16. The electrosurgical system as in claim 12, wherein each candidate frequency satisfies the coherent sampling condition:

$$\frac{f_{in}}{f_s} = \frac{M_{cycles}}{N_{samples}}$$

where fin is a frequency of the output RF energy, fs is a sampling frequency, Mcycles is the number of cycles in a sample set or in a sample window, and Nsamples is the number of samples in the sample set or in the sample window.

17. The electrosurgical system as in claim 14, wherein the controller is configured to set the frequency of the band pass filter to the selected frequency and to filter the feedback signal by the band pass filter using the selected frequency.

18. The electrosurgical system as in claim 12, wherein the controller is configured to calculate an impedance (Z) at the output of the electrosurgical system from the feedback signal, and to control, based on the calculated impedance, an output electric current (I) of the electrosurgical system, or an output electric voltage (V) of the electrosurgical system site, or an electrical power (P) of the RF energy output by the electrosurgical system, or a state of the electrosurgical system, or an operational mode of the electrosurgical system.

19. A method of mitigating interferences during operation of an electrosurgical system, comprising:
by an electrosurgical system configured to output a therapeutic radio frequency (RF) energy, performing,
refraining from outputting RF energy and measuring an RF interference for a group of candidate frequencies;
selecting a frequency from the group of candidate frequencies for which the measured RF interference is below a threshold value;
producing a feedback signal at the selected frequency; and
controlling operation of the electrosurgical system by using the feedback signal.

20. The method as in claim 19, wherein controlling the operation of the electro surgical system comprises: controlling an output electrical current of the electrosurgical system or an output electrical voltage of the electrosurgical system or an electrical power of the RF energy, or transitioning the electrosurgical system between an interrogation mode of operation in which the electrosurgical system outputs an impedance interrogation signal, and a treatment mode of operation in which the electrosurgical system outputs therapeutic RF energy, or controlling a state or an operational mode of the electrosurgical system.

* * * * *